United States Patent [19]

Armstrong et al.

[11] Patent Number: 4,553,933
[45] Date of Patent: Nov. 19, 1985

[54] FORCE-ADJUSTABLE AND DISCONNECTIBLE CONNECTOR FOR ORTHODONTIC HEADGEAR

[75] Inventors: Maclay M. Armstrong, 17001 - 14th Northwest, Seattle, Wash. 98177; Steven A. Houser, Everett, Wash.

[73] Assignee: Maclay M. Armstrong, Seattle, Wash.

[21] Appl. No.: 573,100

[22] Filed: Jan. 23, 1984

[51] Int. Cl.⁴ .............................................. A61C 7/00
[52] U.S. Cl. ...................................................... 433/5
[58] Field of Search ............................................ 433/5

[56] References Cited

U.S. PATENT DOCUMENTS

| | | | |
|---|---|---|---|
| 3,526,035 | 9/1970 | Armstrong | 433/5 |
| 4,115,921 | 9/1978 | Armstrong | 433/5 |
| 4,121,341 | 10/1978 | Dewoskin | 433/5 |
| 4,155,161 | 5/1979 | Armstrong | 433/5 |
| 4,226,589 | 10/1980 | Klein | 433/5 |
| 4,238,188 | 12/1980 | Armstrong | 433/5 |
| 4,368,039 | 1/1983 | Armstrong | 433/5 |
| 4,416,625 | 11/1983 | Armstrong | 433/5 |

Primary Examiner—Robert Peshock
Attorney, Agent, or Firm—Robert W. Beach; Ward Brown

[57] ABSTRACT

A connector for orthodontic headgear includes a casing for a helical compression spring one end of which engages the head of a rod extending through the spring. The other end of the spring engages a sleeve supported in an aperture in the end of the casing. Such casing aperture has a straight chordal portion and the sleeve has axially spaced circumferential flanges with chordally truncated portions for enabling the sleeve to be moved axially relative to the casing flange when in one rotative position for adjusting the spring force and rotatively adjustable relative to the casing flange to hold the sleeve in a selected adjusted position. The connection is disconnectible by providing a metal clip securable to a headcap having legs engageable in grooves in the casing.

9 Claims, 16 Drawing Figures

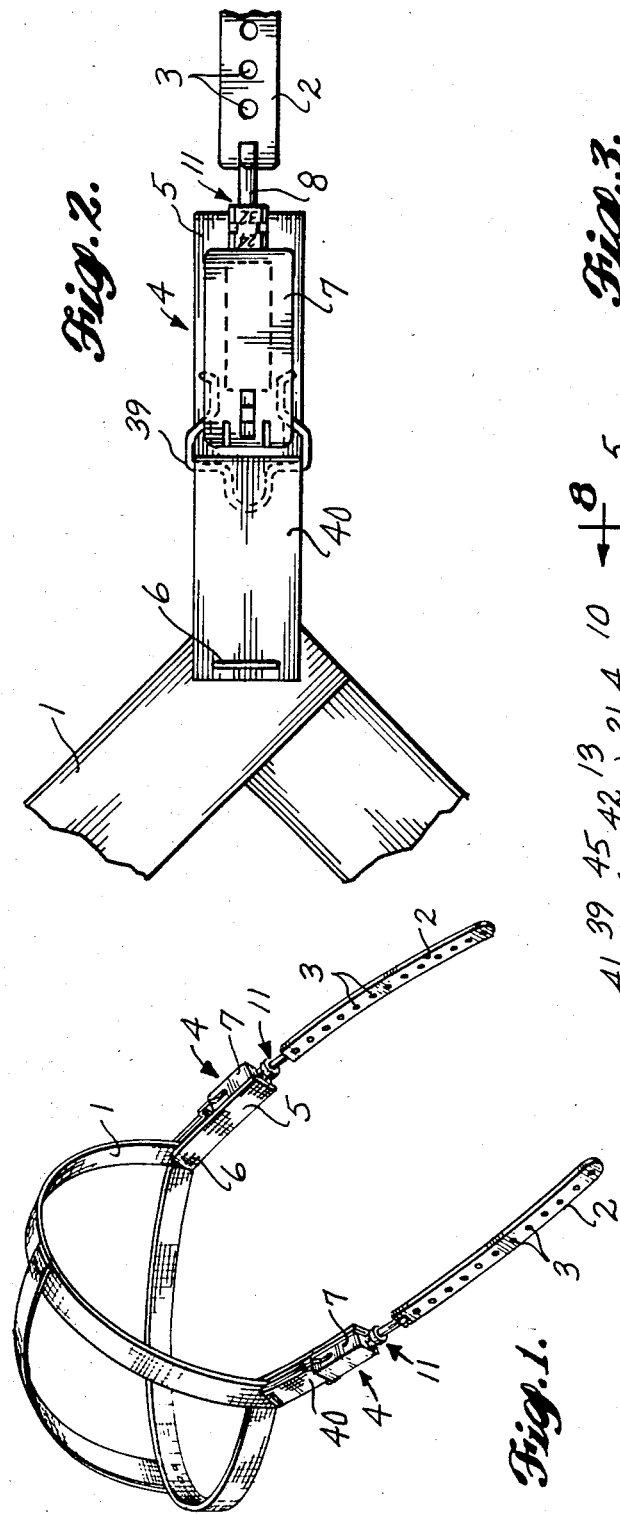
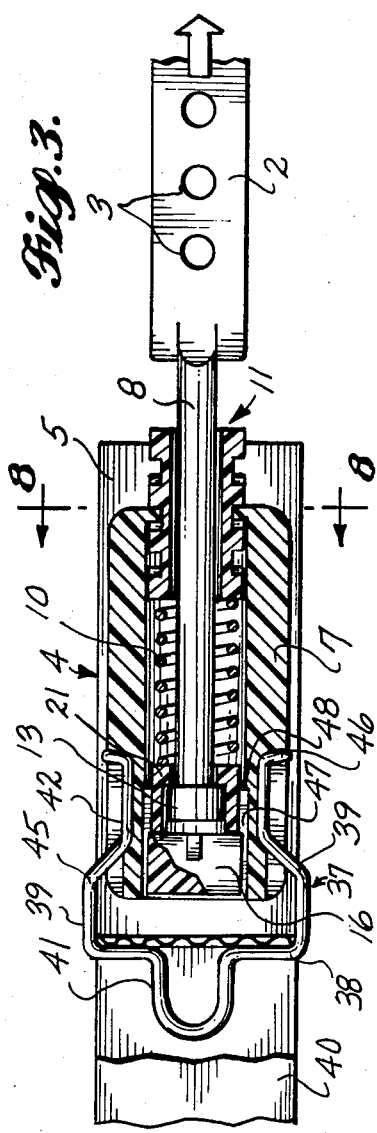

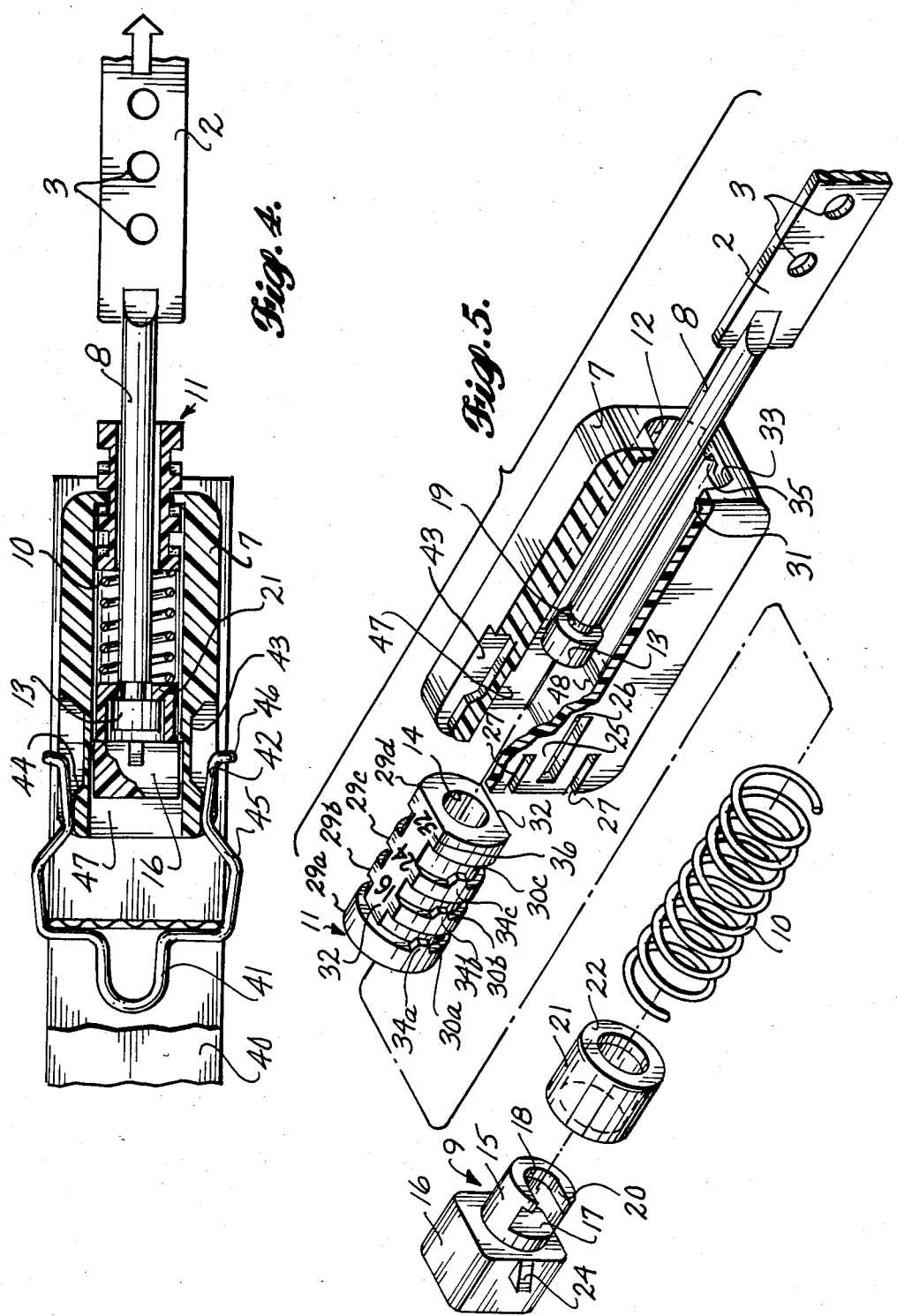

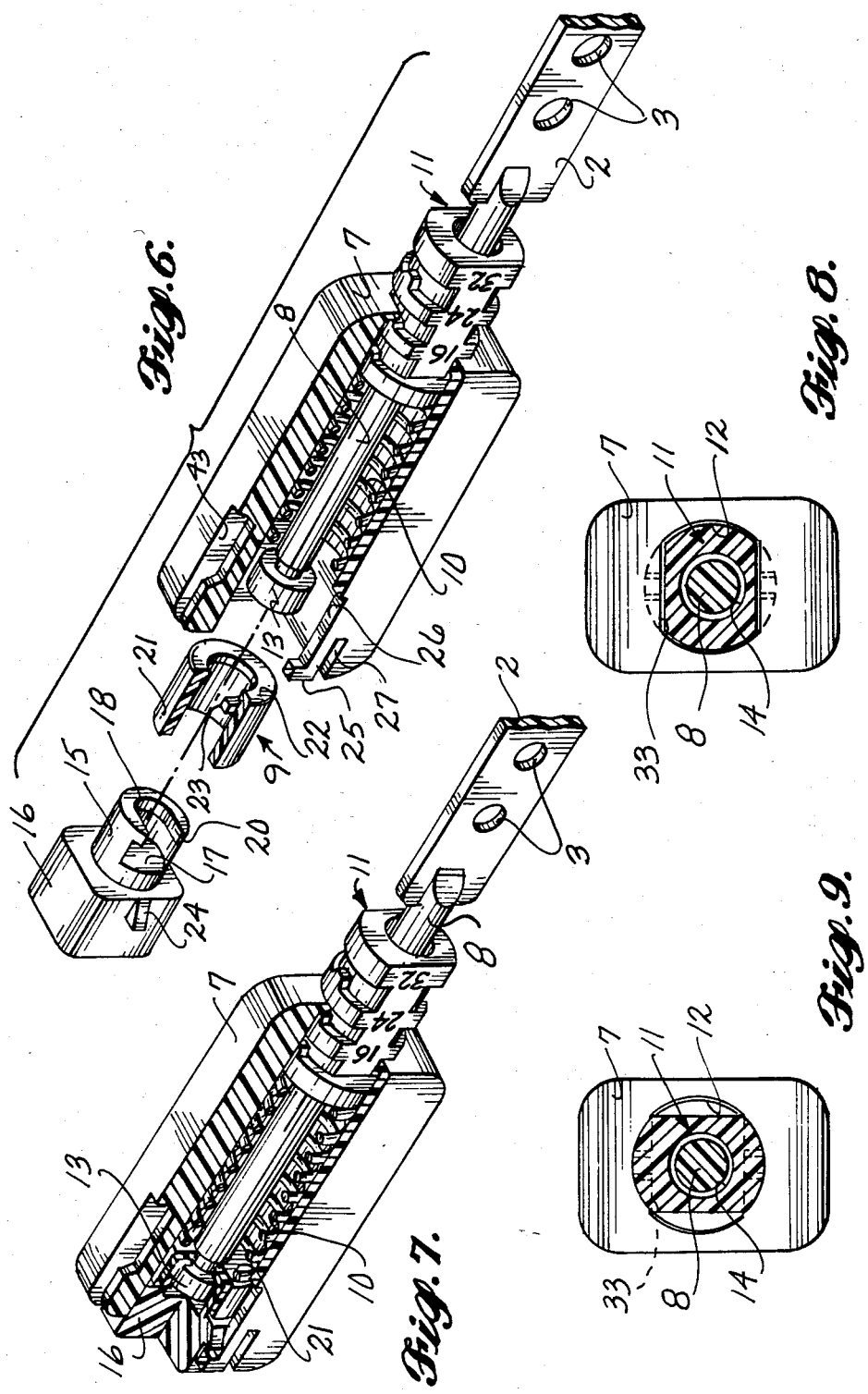

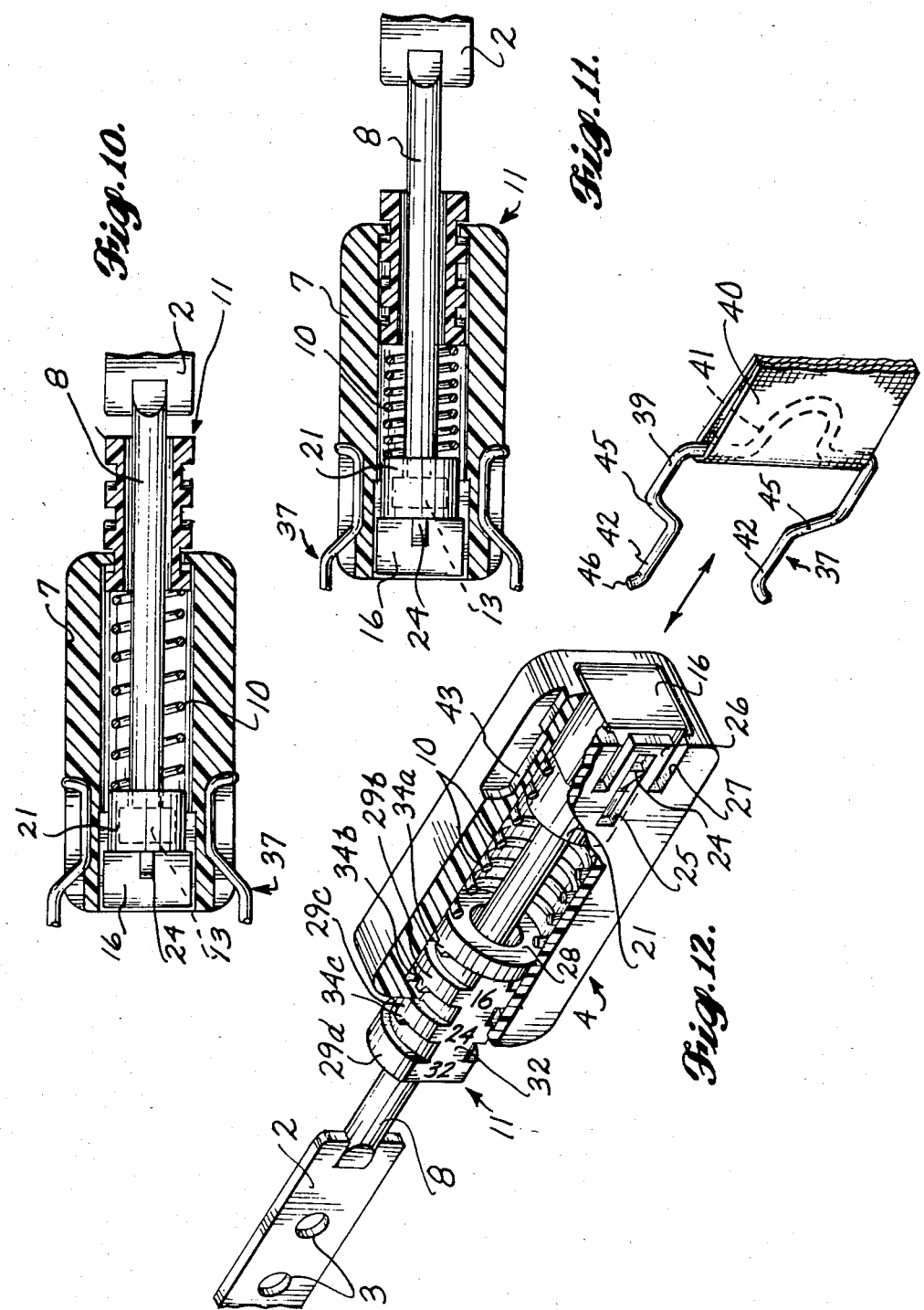

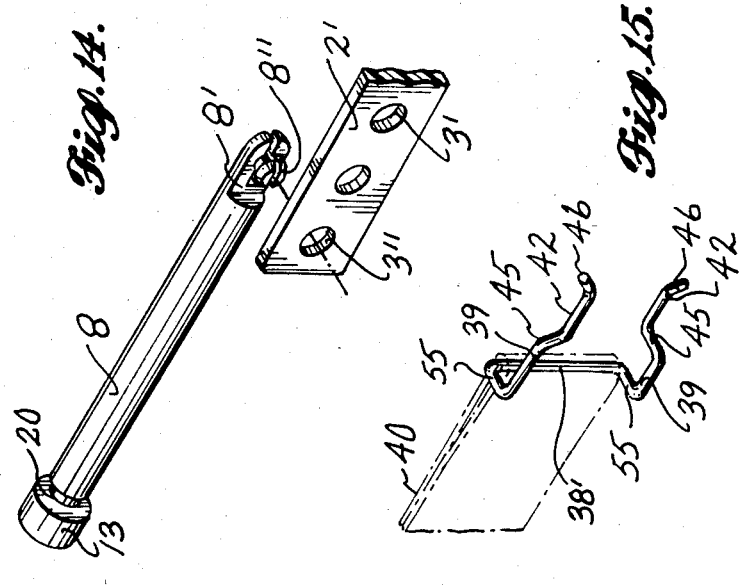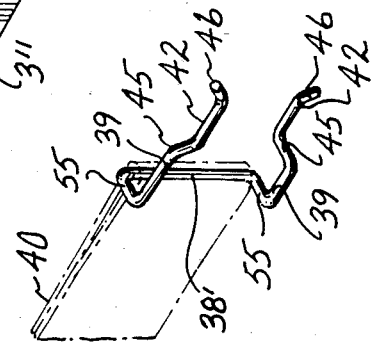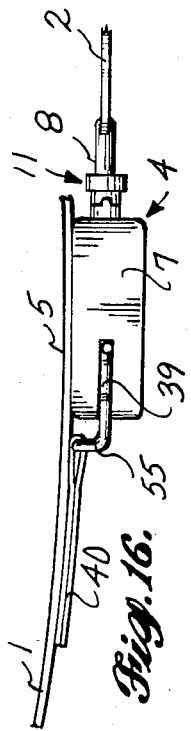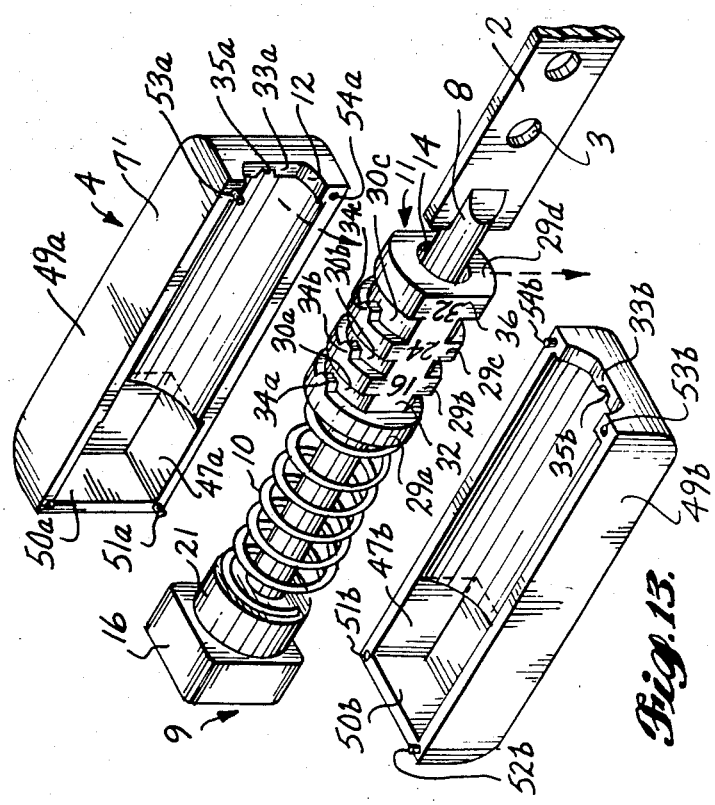

FORCE-ADJUSTABLE AND DISCONNECTIBLE CONNECTOR FOR ORTHODONTIC HEADGEAR

BACKGROUND OF THE INVENTION

1. Field of the Invention

This invention relates to orthodontic headgear, and more particularly to a connector for exerting extraoral force from such headgear to the jaw of the wearer, which connector can be adjusted to provide extraoral force of different degrees and which connector is disconnectible if a force exceeding a predetermined force is exerted on it.

2. Prior Art

Armstrong U.S. Pat. No. 3,526,035, issued Sept. 1, 1970, discloses an orthodontic headgear including a spring which produces an extraoral force the degree of which force is indicated by calibrations.

Later Armstrong U.S. Pat. Nos. 4,115,921, issued Sept. 26, 1978, and 4,155,161, issued May 22, 1979, show extraoral headgears for producing an extraoral force including connectors which are disconnectible when a force exceeding a predetermined force is exerted on them.

Klein U.S. Pat. No. 4,226,589, issued Oct. 7, 1980, discloses a disconnectible orthodontic headgear connector including a return bent spring clip forming a disconnectible connector. The force produced by such connector, however, results from an elastic band or a spring of cross-leg type which is unsatisfactory. Moreover, the travel of the disconnectible parts prior to disconnection is excessive, the minimum force which will effect disconnection is difficult to establish precisely, and the value of such force cannot be altered.

The still later Armstrong U.S. Pat. No. 4,238,188 issued Dec. 9, 1980, discloses a disconnectible connector employing a compression spring for producing an orthodontic force with means for adjusting such force and with a disconnectible connection, but such device is of considerable length.

Armstrong U.S. Pat. No. 4,368,039, issued Jan. 11, 1983 and U.S. Pat. No. 4,416,625, issued Nov. 22, 1983, which resulted from a continuation-in-part application of the application maturing into U.S. Pat. No. 4,368,039, disclose a different type of mechanism for adjusting the extraoral force produced by an orthodontic headgear connector.

Also a disconnectible connector incorporating a helical compression spring is shown in the publication High-Pull Traction Release System of Unitek Corporation bearing the copyright notice date of 1979.

SUMMARY OF THE INVENTION

A principal object of the present invention is to provide a connection for orthodontic headgear having advantages of prior orthodontic headgear connectors embodied to some extent in the devices shown in the patents referred to above, namely, spring mechanism for producing an extraoral force, indicating means for indicating the force being exerted, means to adjust the degree of force produced by the force-producing mechanism and disconnectible mechanism for effecting disconnection of the connector by exertion on the connector of a force greater than a predetermined force, while at the same time making the connector compact, neat in appearance and precise in operation.

It is also an object to provide such a connector in which the working mechanism will be concealed to as great an extent as possible and which can present access to such working mechanism so as to be tamperproof.

Another object is to provide an adjustment by which the force-producing mechanism can be altered easily, quickly and reliably to enable the orthodontic headgear to exert different degrees of extraoral force on the jaw of the wearer.

The foregoing objects can be accomplished by a connector having a casing in which a helical compression spring is housed that exerts an extraoral traction force on a plunger. An abutment against which one end of the spring bears can be shifted axially of the spring relative to the casing to alter the length of the spring stroke permitted. A return bent spring clip that can be arranged to clamp one end portion of the casing will be pulled away from the casing by exertion on the connector of a force exceeding a predetermined force.

BRIEF DESCRIPTION OF THE DRAWINGS

FIG. 1 is a top perspective of an orthodontic headcap including two connectors of the present invention.

FIG. 2 is a side elevation of a connector according to the present invention.

FIG. 3 is a longitudinal section through the connector of FIG. 2 on an enlarged scale, and FIG. 4 is a similar section showing parts in different positions.

FIG. 5 is a top perspective of the connector showing components in exploded relationship and with parts broken away, and FIG. 6 is a similar top perspective with certain components shown in assembled relationship and other components shown in exploded relationship parts being broken away.

FIG. 7 is a top perspective of the connector with more components shown in assembled relationship but having parts broken away.

FIG. 8 is a transverse section taken on line 8—8 of FIG. 3, and FIG. 9 is a similar section but showing components in a different relationship.

FIG. 10 is an enlarged fragmentary section similar to FIG. 3 but showing components in a different relationship, and FIG. 11 is a similar fragmentary section showing components in still a different relationship.

FIG. 12 is a top perspective of the connector turned end-for-end from FIG. 7, having parts broken away and illustrating one component in exploded relationship.

FIG. 13 is a top perspective of a modified form of the connector showing parts in exploded relationship.

FIG. 14 is a top perspective of a modified component of the connector, shown in exploded relationship with respect to another component of the headgear.

FIG. 15 is a top perspective of another modified component of the headgear, and FIG. 16 is a plan of the connector incorporating the modified component shown in FIG. 15.

DETAILED DESCRIPTION

Two connectors according to the present invention can be connected between opposite sides, respectively, of an orthodontic headgear headcap 1 made of nonstretchable fabric or webbing and side straps 2 made of flexible plastic having apertures 3 at regularly spaced intervals along their lengths for engagement with hooks on opposite ends of an orthodontic facebow or chin cup. The straps are connected to a face bow or chin cup for applying force of a spring in the connector to the wearer's jaw and the headcap or a neckband applies a reaction force to the wearer's head. The cheeks of the wearer can be protected from contact by the connectors 4 by tabs 5 of a webbing having one end anchored by a staple 6 or by sewing to a side of the headcap and projecting from the headcap downward and forward along the side of the wearer's head.

The connector includes principally an elongated casing 7 made of suitable plastic material such as nylon within which a plunger reciprocates to exert force on the strap 2. The plunger includes a rod 8 having on its end remote from the strap 2 a composite head 9. The force-producing helical compression spring 10 is engaged between such head and the end of a sleeve 11 which is adjacent to the spring when the connector is assembled. Such sleeve is lodged in an aperture 12 in the end of casing 7 adjacent to strap 2.

The composite plunger head 9 includes a knob 13 on the end of rod 8 remote from strap 2 which is of a size to slide in close-fitting relationship through the bore 14 of sleeve 11. Such knob can be coupled with a boss 15 of a slide 16 by being moved transversely of the length of rod 8 into a socket 17 within such boss through a side opening gate. The end of the cavity in boss 15 remote from slide 16 has an internal flange 18, the inner edge of which fits into the neck 19 formed as an annular groove in rod 8 at the base of knob 13. Such flange can enter the neck groove because of the gate 20 in such flange in registration with the lateral opening into socket 17 of boss 15.

The knob 13 is retained in the socket 17 of boss 15 by a keeper collar 21 having a bore of a size to fit slidably over the boss. The end of such collar remote from the slide 16 has an internal flange 22 with an aperture of a size to fit slidably over the knob 13. A lug 23 projecting inwardly from the interior of the collar adjacent to flange 22 is of an axial width corresponding to the thickness of flange 18 of boss 15 and of a circumferential extent corresponding to the gate 20 of such flange.

In assembling the components of the connector from their exploded relationship shown in FIG. 5 to their partially assembled relationship shown in FIG. 6, the knob or head 13 of the stem 8 is first inserted through the bore 14 of sleeve 11 and then through the end aperture 12 of casing 7. At such time the sleeve 11 may or may not have been installed in the aperture 12 of casing 7 depending on the length of the rod 8.

Next compression spring 10 is slid over the knob 13 and that portion of the rod 8 projecting beyond the end of sleeve 11 remote from the strap 2. The flange 22 of collar 21 will then be slid over the knob 13 compressing spring 10 between collar 21 and sleeve 11 as necessary to enable the knob to project beyond the end of casing 7 remote from its aperture 12. In that position, the boss 15 of slide 16 can be moved transversely of the length of rod 18 to slide the boss over the knob so that it is lodged in cavity 17 of the boss and flange 18 is fitted into the neck groove 19 of the rod. The force-compressing spring 10 can then be relieved to enable such spring bearing on flange 22 of collar 21 to slide such collar over boss 15 of slide 16 and move lug 23 into the gate 20 of flange 18.

With the internal components of the connector thus assembled, sleeve 11 is fitted into aperture 12 of casing 5 if it is not already in such position. Strap 2 can then be pulled so that the composite head of the plunger composed of knob 13, slide 16 and collar 21 can be urged against the adjacent end of compression spring 10, the opposite end of which abuts the adjacent end of sleeve 11, until the end of slide 16 begins to enter the open end of casing 7. During such manipulation, the noncylindrical slide 16, which is of generally square profile, will be rotatively oriented to fit the open end of the casing. In such position a lug 24 projecting from one side of the slide and tapered toward the casing will engage a tongue 25 having in it a slot 26 elongated lengthwise of the elongated casing 7 and parallel to the rod 8. The tongue is made of resilient material such as hard plastic and is formed between parallel blind or open-ended slots 27 in the casing wall at opposite sides of the tongue so that such tongue extends in cantilever fashion toward the open end of casing 7.

As the strap 2 is pulled to draw slide 16 into the open end of casing 7, the tapered lug 24 will wedge the flexible tongue 25 outwardly until such lug comes into registration with the slot 26, whereupon the tongue will snap back toward the cavity of the casing. The tongue 25 and lug 24 thus form a catch limiting movement of the slide outward from the cavity of the casing, constituting a snapback travel limit, which catch retains the internal components of the connector in their assembled relationship shown in FIG. 7.

The orthodontic force which will be exerted by spring 10 on strap 2 will depend upon the degree to which such spring is compressed between the flange 22 of the plunger rod 8 and the abutment face 28 of sleeve 11 engaged by one end of the spring i.e. the effective length of the spring, which in turn will depend upon the position of the sleeve 11 and the casing 7 longitudinally of the lengthwise relationship between the plunger head 9 and the casing. When a pull is not being exerted on rod 8, the travel of the plunger head away from sleeve 11 will be limited by engagement of the catch lug or lugs 24 with the end of slot or slots 26 remote from sleeve 11. The minimum force exerted by the spring can be regulated by establishing the relationship of sleeve 11 relative to the casing 7 longitudinally of the spring and rod 8. The construction of the connector enables the longitudinal position of the sleeve relative to the casing to be altered so as to be able to adjust selectively the minimum degree of force exerted by the spring when the rod is in such position relative to the casing.

To enable the degree of spring force applied to the headcap 1 and the strap 2 to be adjusted the force-setting sleeve 11 shown in FIGS. 3 to 12 has latch means including as a first component axially spaced annular flanges 29a, 29b, 29c and 29d separated by axially spaced annular grooves. The groove 30a is located between adjacent flanges 29a and 29b, the groove 30b is located between adjacent flanges 29b and 29c and the groove 30c is located between adjacent flanges 29c and 29d.

The aperture 12 in the end of casing 7 in which the sleeve 11 is lodged is formed by an internal flange 31 of varying radial width constituting a second component of the latch means. The annular flanges 29b, 29c and 29d of sleeve 11 are not of full circular cross section, but are interrupted, their diametrically opposite sides being truncated to form diametrically opposite chordal surfaces 32. Correspondingly, casing aperture 12 is not circular but its diametrically opposite sides 33 are chordal complemental to the opposite sides of the sleeve flanges 29b, 29c and 29d. As shown in FIG. 8, therefore, when the sleeve 11 is turned into the proper rotative position relative to the noncircular casing aperture 12, the sleeve 11 can slide outward through such aperture from the interior of the casing until opposite portions of the circular flange 29a engage the inner surface of casing flange 31 adjacent to the chordal flange portions 33. When the sleeve 11 has been moved axially relative to the casing to place a selected annular groove 30a, 30b or 30c in registration with a casing flange 31, the sleeve and casing may be turned relatively through an angle of 90 degrees to alter the relationship of the casing and sleeve from that shown in FIG. 8 to that shown in FIG. 9 for latching the sleeve to the casing.

The axial widths of grooves 30a, 30b and 30c are greater than the thickness of casing flange 31, and may be approximately twice as great as such flange thickness, so that sleeve 11 can be moved axially relative to casing 7 to a limited extent even when the sleeve and casing aperture 12 are in the relative positions shown in FIG. 9. To maintain the sleeve and casing in such relative rotative positions against inadvertent circumferential displacement teeth 34a, 34b and 34c are provided in the respective annular grooves 30a, 30b and 30c of sleeve 11. Such teeth project axially into the grooves from the groove sides remote from strap 2 and adjacent to spring 10 in the direction away from such spring. Such teeth preferably are tapered away from their roots and are of a profile complemental to the profile of a notch or notches 35 located in a chordal side, or both chordal sides, of the aperture 12 in casing flange 31. When the sleeve 11 is in the rotative position relative to casing 5 shown in FIG. 9, therefore, the tooth of the groove in which flange 31 is fitted will mesh with a notch 35. The force exerted by spring 10 against the end 28 of sleeve 11 will press the sleeve in a direction to maintain its tooth engaged with the flange notch to prevent relative rotation of the sleeve and casing.

One or both of the chordal surfaces 32 are labeled at the locations of the respective annular flanges 29b, 29c and 29d with designations 36 indicating the orthodontic force produced by compression spring 10 corresponding to the axial position of sleeve 11 in casing aperture 12. FIG. 5 shows number 16 in registration with flange 29b, number 24 in registration with flange 29c and number 32 in registration with flange 29d. These numbers represent ounces of orthodontic force produced by the spring 10.

When the sleeve 11 is in the position relative to casing 7 shown in FIG. 10, the number 16 will be visible adjacent to the end of the casing. With the components in this position, the number 16 indicates that an orthodontic force of 16 ounces will be exerted on strap 2 when that strap is pulled so that the outer face of slide 16 is substantially flush with the adjacent end of casing 7, as shown in FIG. 10. When the sleeve 11 is adjusted axially relative to casing 7 to the position shown in FIG. 3 in which annular groove 30b is in registration with casing flange 31, the number 24 on chordal surface 32 will be seen adjacent to the end of casing 7. Such designation indicates that an orthodontic force of 24 ounces will be exerted when strap 2 is pulled so that the outer end of slide 16 is substantially flush with the adjacent end of the casing, as shown in FIG. 3. When the sleeve 11 has been adjusted axially relative to the casing 7 to the position shown in FIG. 11, the number 32 on the chordal surface 32 will be visible adjacent to the apertured end of casing 7. With the sleeve in this position of adjustment, the orthodontic force produced when the strap is pulled sufficiently to place the outer end of slide 16 substantially flush with the open end of casing 7, as shown in FIG. 11, will be 32 ounces.

In order to exert an orthodontic force on a strap 2, it is necessary for casing 7 to be connected to a reaction member such as the headcap 1 or a neckstrap. It is, however, desirable for safety purposes to have the connection between the strap 2 and the headcap 1 be disconnectible if a pull greater than a predetermined force is exerted on a strap 2, for reasons discussed in detail in the Armstrong prior U.S. Pat. Nos. 4,115,921 and 4,155,161. Disconnection of the present connector is afforded by a clip 37 arranged to clamp casing 7, as shown best in FIGS. 2 and 3. Such clip is preferably made of resilient metal and includes a cross member 38 from opposite ends of which project generally parallel legs 39. The cross member can extend through a loop 40 of fabric carried by the headcap 1, or a neckstrap, which extends generally parallel to and overlaps the protective fabric tab 5, as shown in FIG. 2. To enable the attitude of the clip to be controlled more readily, its transverse member 38 may include a central loop handle 41 fitted between the parts of the fabric loop 40, as shown in FIG. 12.

The generally parallel clip legs 39 include clamping portions 42 offset toward each other and preferably disposed in parallel relationship when they are in clamping engagement with casing 7. Such clamping portions of the clip legs can engage in grooves 43 formed in the opposite sides of the casing. Such grooves include portions of a length equal to the length of the clip clamping portions 42 so that there is no endwise play between the clip and the casing. Such slot portions have shoulders 44 at their ends closer to the adjacent end of the casing 7 and the offset clamping portions 42 of the clip legs 39 have converging leg portions 45 adjacent to them engageable with such shoulders. The tips of the generally parallel clip legs are bent oppositely outward, as shown in FIGS. 3 and 4.

The slide 16 is slidable snugly in the cavity 47 formed by the open end of the casing 7. Inward movement of such slide is limited to the position shown in FIG. 4 by engagement of the inner end of such slide with a circumferential shoulder 48 in the casing cavity. Travel of the plunger lengthwise of rod 8 is therefore limited in one direction by engagement of a lug 24 with the end closer to the adjacent end of the casing of a slot 26 in which it is engaged and in the opposite direction by engagement of the inner end of slide 16 with casing shoulder 48.

Increasing the pull on strap 2 relative to casing 7 will draw rod 8 progressively out of the casing until the inner end of slide 16 bottoms on shoulder 48. Such engagement will terminate travel of rod 8 out of the casing. If the pull on strap 2 continues to increase, the force between shoulders 44 and the convergent portions 45 of the legs of clip 37 will wedge the clip legs apart until the casing-engaging portions 42 slide over the casing shoulders 44, as shown in FIG. 4. Such movement will effect disconnection of the clip from the casing.

Separating movement of the clip legs from the attitude of FIG. 3 to the attitude of FIG. 4 is very small because the casing shoulders 44 are rather abrupt and not very high. Consequently, the clip will maintain its position shown in FIG. 3 until the predetermined limiting force has been reached, whereupon the clip legs will be wedged apart to the attitude shown in FIG. 4 instantaneously and disconnection will occur with virtually no possibility of the resilience of the clip restoring its legs to the positions of FIG. 3 once they have been wedged apart appreciably. To reconnect the clip with the connector body 7, it is merely necessary to push the outturned tips 46 into the casing grooves 42 in the manner illustrated in FIG. 12, whereupon the tips will wedge the clip legs apart so that they can enter their respective grooves 43 and restore the connector to its connected condition shown in FIG. 3.

The amount of pulling force on strap 2 that can be tolerated before the connector will disconnect depends on the clamping force exerted by the clip 37 on the connector casing 7. Such clamping force can be determined by the selection of the material of the clip 37 as to type of metal, cross-sectional size of the clip stock and tempering of the metal.

It is possible to disassemble the components of the connector described above by wedging outward the free ends of tongues 25 until the catch lugs 24 are freed from slots 26. It is possible, however, to provide a connector which is tamperproof by enclosing the working parts of the connector in a sealed casing. The casing 7' is incorporated in the modified connector shown in FIG. 13. The working components of this connector are substantially identical to those described in connection with FIGS. 3 to 12 but, in this instance, the casing 7' is formed of two complementary halves 49a and 49b. Instead of the casing being open at the end opposite the aperture 12, such end is closed by cooperating end wall sections 50a and 50b. The working mechanism can be assembled outside of the casing and then the casing halves assembled over it so that the slide 16 will be received half in the casing cavity 47a and the other half in the casing cavity 47b.

Registration of the casing halves in assembling them will be ensured by peg 51a in one corner of section 49a fitting in socket 51b of the corresponding corner of section 49b, socket 52a in another corner of section 49a fitting over peg 52b in the corresponding corner of section 49b, peg 53a in another corner of section 49a fitting into socket 53b in a corresponding corner of section 49b and socket 54a in the other corner of section 49a fitting peg 54b in the corresponding corner of section 49b. A suitable adhesive can be used to bond together the matching edges of the two casing sections to prevent their disassembly.

The head 9 of the rod 8 in FIG. 13 could be made in a single piece if the rod 8 and strap were made separately and connected by a joint such as illustrated in FIG. 14. The end of rod 8 remote from head 9 or knob 13 has an end portion 8' of reduced width carrying a button or headed pin 8" that can be forced through the end opening 3" of a side strap 2' having additional spaced apertures 3' arranged along its length. The button or headed pin and aperture 3" preferably are constructed so that the parts can be disassembled without mutilating either the button or the buttonhole, but these components should be connected sufficiently securely so that they will not become separated inadvertently.

In order to minimize cocking of the connector casing 7 where the loop 40 is provided in a neckstrap, the clip may have an offset cross member of the type shown in FIGS. 15 and 16. The generally parallel legs of the clip may be like those described in connection with FIGS. 3 and 4 including parts 39 from which sections 45 converge inwardly to the casing clamping portions 42 that have outturned tips 46. Instead of the leg sections 39 being connected directly by a cross member, however, offsetting sections 55 connect the sections 39, respectively, to the opposite ends of a cross member 38'. Such cross member is not shown as having a handle loop such as 41, but it could be provided with such a handle loop if desired.

The length of offsetting sections 55 is equal to approximately one-half the thickness of the casing 7, as shown in FIG. 16, so that when the connecting section 38' is received in loop 40 and the clip and casing are in assembled relationship, the loop and casing will not be cocked appreciably even though the casing grooves in which the clip legs are engaged are located substantially in the center of the casing and parallel to the opposite sides of the casing.

We claim:

1. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, abutment means engageable by the spring and adjusting means for altering the effective spring length and consequently the force produced by the spring on the force-reaction means and the force-applying means by supporting the abutment means in different positions axially of the spring, the improvement comprising latch means including a first component carried by the abutment means and movable therewith axially of the spring and a second component latchingly engageable with said first component by relative turning of said first and second components about the axis of the spring for limiting movement of the abutment means axially of the spring.

2. The connector defined in claim 1, including a casing carrying the second latch means component, and the abutment means is a sleeve carrying the first latch means component and engageable by one end portion of the spring.

3. The connector defined in claim 2, in which the casing has an aperture with an internal flange, and the sleeve has a plurality of annular grooves spaced axially of the spring and selectively engageable with said flange.

4. The connector defined in claim 2, in which the casing has an aperture with curved sides and a straight chordal portion, and the sleeve has an annular flange with a chordally truncated portion corresponding to said straight chordal portion of said casing aperture for enabling the sleeve to move through said casing aperture when said chordally truncated portion of said flange is in registration with said straight chordal portion of said casing aperture, and the sleeve and casing being turnable relatively for movement of said chordally truncated portion of said flange out of registration with said straight chordal portion of the casing aperture to retain the sleeve against movement axially of the spring relative to the casing.

5. The connector defined in claim 3, in which each annular sleeve groove has a tooth directed lengthwise of the spring and the casing internal flange has a notch for reception of said tooth to deter relative circumferential displacement of the sleeve and casing while said tooth is engaged in said casing flange notch.

6. A force-producing connector for orthodontic headgear including force-reaction means engageable with the head or neck of a wearer, force-applying means for applying force to the wearer's jaw, a helical compression spring and means for applying force produced by the spring to the force-reaction means and the force-applying means, the improvement comprising a casing having grooves in opposite sides thereof, and a resilient metal clip including a cross member having a handle loop and generally parallel spaced leg members connected to opposite ends of said cross member and received in said casing grooves respectively.

7. The force-producing connector defined in claim 6, in which the cross member includes a transverse member and parallel offsetting members connected to opposite ends thereof and projecting laterally therefrom, and the leg members are connected to the ends of said offsetting members remote from said transverse member for location of the clip leg members in a plane offset from said transverse member.

8. In a force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means and a rod extending axially through the compression spring and having a knob on the end thereof, the improvement comprising a head member having a socket therein opening laterally of the rod for reception of the knob therein by movement relative to said head member transversely of the rod, and a keeper collar encircling the rod adjacent to the knob and extending over said head member for obstructing access to said socket for retaining the knob therein.

9. The connector defined in claim 8, in which an end portion of the spring bears on the keeper collar for holding the collar in a position obstructing the entrance to the head member socket.

* * * * *